United States Patent [19]

Sturla

[11] Patent Number: 5,595,727
[45] Date of Patent: Jan. 21, 1997

[54] AQUEOUS COSMETIC COMPOSITION FOR SETTING THE HAIR BASED ON THE COMBINATION OF HYDRODISPERSIBLE POLYCONDENSATE AND A HYDROSOLUBLE COPOLYMER

[75] Inventor: Jean-Michel Sturla, Saint-Cloud, France

[73] Assignee: L'Oreal, Paris, France

[21] Appl. No.: 447,171

[22] Filed: May 19, 1995

[30] Foreign Application Priority Data

May 19, 1994 [FR] France ................... 94-06119

[51] Int. Cl.$^6$ ........................................ A61K 7/08
[52] U.S. Cl. ............. 424/47; 424/70.11; 424/78.03; 424/DIG. 1; 424/DIG. 2
[58] Field of Search ............... 424/47, DIG. 1, 424/DIG. 2, 401, 70.11, 70.15, 70.16, 70.17, 78.03

[56] References Cited

U.S. PATENT DOCUMENTS

| | | | |
|---|---|---|---|
| 4,282,203 | 8/1981 | Jacquet et al. | 424/47 |
| 5,158,762 | 10/1992 | Pierce | 424/47 |
| 5,266,303 | 11/1993 | Myers et al. | 424/47 |

FOREIGN PATENT DOCUMENTS

| | | |
|---|---|---|
| 2439798 | 5/1980 | France. |
| 9311736 | 6/1993 | WIPO. |

*Primary Examiner*—John C. Bleutge
*Assistant Examiner*—Robert H. Harrison
*Attorney, Agent, or Firm*—Cushman Darby & Cushman Intellectual Property Group of Pillsbury Madison & Sutro LLP

[57] ABSTRACT

A cosmetic composition for setting the hair contains, in an aqueous or weakly hydroalcoholic medium, (a) 0.5 to 40 percent by weight relative to the total weight of the composition of a hydrodispersible polycondensate having sulfonate functions, and (b) 0.5 to 15 percent by weight relative to the total weight of the composition, of a hydrosoluble copolymer having at the same time patterns derived from vinyl acetate, at least one monomer having a neutralized carboxylic acid function and at least one monomer having cyclic ester function, the total neutralization amount of the said copolymer being greater than 80 percent. This composition exhibits excellent setting power while being removed very satisfactorily by washing with a shampoo.

17 Claims, No Drawings

AQUEOUS COSMETIC COMPOSITION FOR SETTING THE HAIR BASED ON THE COMBINATION OF HYDRODISPERSIBLE POLYCONDENSATE AND A HYDROSOLUBLE COPOLYMER

The present invention has for an object a cosmetic composition for setting hair containing in an aqueous or weakly hydroalcoholic medium, a combination of a hydrodispersible polycondensate having sulfonate functions and a hydrosoluble copolymer constituted by at least units having a neutralized carboxylic acid function and by units having a cyclic ester function.

For several years, a quite particular interest has been manifested for the production of essentially aqueous capillary cosmetic compositions. In effect, the use of an alcohol, such as ethanol or isopropanol, alone or in admixture with a small amount of water, can present certain disadvantages, principally an inflammable increase when the composition is in an aerosol lacquer form.

The use of a strong amount of water requires a particular selection of filmogen resins compatible with the medium and susceptible to convey to the cosmetic properties analogous to those of compositions having a strong content in alcohol to know good diffusion during application, rapid evaporation of the solvent, good setting power, humidity resistance and good removal during shampooing.

In U.S. Pat. No. 5,158,762, there has been proposed, with the intention of obtaining cosmetic properties comparable to those of compositions having strong alcohol content, aqueous compositions for setting the hair. Such compositions comprise a mixture of at least one hydrodispersible resin consisting of a polycondensate having sulfonate functions and a hydrosoluble resin consisting between others in a vinyl acetate/crotonic acid or vinyl acetate/crotonic acid/vinyl neodecanoate copolymer.

However, the removal of the filmogen resin by washing, employing a conventional shampoo, has been considered little satisfactory.

It has now been ascertained in a surprising and unexpected manner that it is possible to produce aqueous compositions for setting hair exhibiting excellent setting power while removing in a very satisfactory manner by washing with the aid of a shampoo, by using the combination of a hydrodispersible polycondensate having sulfonate functions and a very particular family of hydrosoluble copolymers having at the same time units derived from vinylacetate, at least one monomer having a neutralized carboxylic acid function and at least one monomer having a cyclic ester function.

The present invention has then for an object an aqueous cosmetic composition for setting the hair containing in an aqueous or slightly hydroalcoholic medium:

(a) 0.5 to 40 weight percent relative to the total weight of the composition, a hydrodispersible polycondensate having sulfonate functions, and (b) 0.5 to 15 weight percent relative to the total weight of the composition a hydrosoluble copolymer having the formula

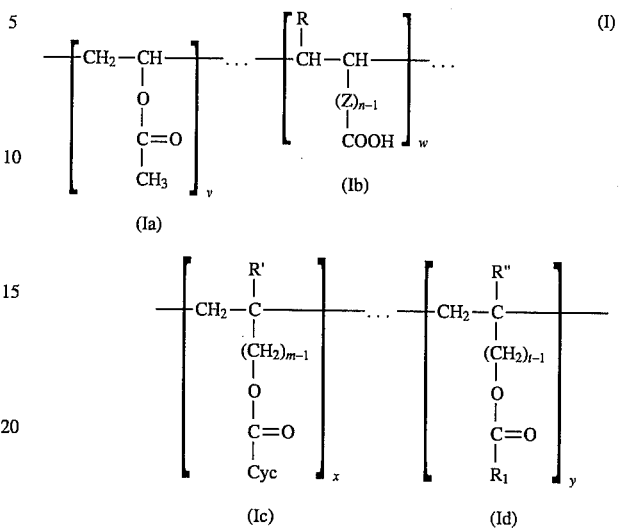

wherein

R, R' and R", each independently, represent hydrogen or methyl, m, n and t are 1 or 2, $R_1$ represents linear or branched, saturated or unsaturated alkyl having 2 to 21 carbon atoms, Z represents a divalent radical selected from the group consisting of $-CH_2-$, $-CH_2-O-CH_2$ and $-CH_2O-(CH_2)_2-$ and Cyc represents a member selected from the group consisting (i)

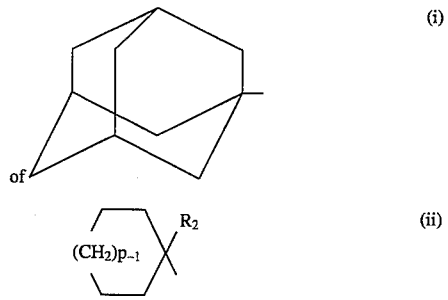

(ii)

wherein $R_2$ represents hydrogen or methyl and p is 1 or 2,

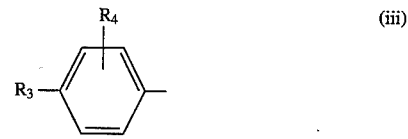

(iii)

wherein $R_3$ represents hydrogen, methyl, ethyl, tert-butyl, ethoxy, butoxy or dodecyloxy and $R_4$ represents hydrogen, alkyl having 1–4 carbon atoms or alkoxy having 1–4 carbon atoms, and

(iv)

v represents 10 to 90 percent and preferably 36 to 84 weight percent, w represents 3 to 20 percent and preferably 6 to 12 weight percent, x represents 4 to 60 percent and preferably 6 to 40 weight percent, and y represents 0 to 40 percent and preferably 4 to 30 weight percent, v+w+x+y being equal to 100 percent, the said carboxylic acid functions of said copolymer being neutralized by a basic agent in an amount greater than 80 percent.

The simultaneous presence of units (Ic) in combination with units (Ia) and (Ib) in the formula (I) copolymers considerably improve elimination of, during shampooing, capillary compositions, in accordance with the invention, by showing the comparative studies given below.

In accordance with a preferred employment of the compositions, according to the present invention, the amount of the hydrodispersible polycondensate having sulfonate functions is between 2 and 30 weight percent relative to the total weight of the composition and that the hydrosoluble copolymer, such as previously defined, is preferably between 1 and 10 weight percent relative to the total weight of the composition.

Preferably, the weight amount between the hydrosoluble copolymer and the hydrodispersible polycondensate is between 0.15 and 0.6.

According to a particularly preferred production of the present invention this amount ranges from 0.2 to 0.4.

The hydrodispersible polycondensates having sulfonate functions, employed in accordance with the present invention, generally have a vitreous transition temperature between 10° C. and 100° C. and preferably between 25° C. and 60° C.

Hydrodispersible polycondensates having sulfonic functions, principally include, according to the present invention, copolyesters or copolesteramides. The copolyesters are obtained by polycondensation of at least a dicarboxylic acid or one of its esters, at least a diol and at least a difunctional sulfoaryldicarboxylic compound substituted on the aromatic ring by a group —$SO_3M$ wherein M represents hydrogen or a metallic ion such as $Na^+$, $Li^+$ or $K^+$. The copolyesteramides are obtained in the same manner as the copolyesters, but the polycondensation also makes equally intervening a diamine and/or an amino alcohol.

The hydrodispersible polycondensates, such as previously defined, are known and have been described principally in U.S. Pat. No. 3,779,993; U.S. Pat. No. 4,300,580 and EPO 0.540.374.

They generally have an average molecular weight between about 1,000 and 60,000 and preferably about 14,000.

The hydrodispersible copolyesters and copolyesteramides having sulfonate functions, preferably employed according to the present invention, exhibit the common characteristic of including at least units derived from isophthalic acid, dicarboxylic acid salt and diethylene glycol.

According to a particular manner of producing compositions according to the present invention, the hydrodispersible polycondensates having sulfonate functions are copolyesters having units derived from isophthalic acid, the sodium salt of sulfoisophthalic acid, diethylene glycol and 1-4 cyclohexanedimethanol. These units, respectively, are preferred and are present in amounts of 89/11/78/22 or 82/18/54/46. These copolyesters are commercialized under the names of AQ38® and AQ55® by Eastman Kodak.

According to another manner of producing the compositions of the present invention, the hydrodispersible copolyesters employed can additionally contain patterns derived from ethylene glycol, tri-and tetraethylene glycol and terephthalate.

The hydrosoluble copolymer responding to formula (I) preferably has an average molecular weight between 5,000 and $10^6$.

Among the formula (I) copolymers there are included those disclosed in BF 78.30596 and, preferably vinyl acetate/crotonic acid/4-tert.butyl vinyl benzoate (57/10/25/8) copolymer;

vinyl acetate/crotonic acid/4-tert.butyl vinyl benzoate/ vinyl neodecanoate (70/10/10/10) copolymer;

vinyl acetate/crotonic acid/vinyl benzoate/vinyl neodecanoate (70/10/10/10) copolymer, vinyl acetate/crotonic acid/4-tert.butyl vinyl benzoate/ allyl stearate (70/10/10/10) copolymer and vinyl acetate crotonic acid/4-tert.butyl vinyl benzoate (65/10/25) copolymer.

These copolymers are not employed as such in compositions, according to the present invention, but must be previously neutralized to an amount greater than about 80 percent.

Preferably, the hydrosoluble copolymers employed in accordance with the present invention are 100 percent neutralized.

The neutralization of the carboxylic acid functions is carried out using a basic agent selected for example from a mineral base such as soda or potash or an organic base selected from the group consisting of 2-amino-2-methyl-1-propanol (AMP), triethanolamine, triisopropanolamine (TIPA), monoethanolamine, diethanolamine, tri[(2-hydroxy) 1-propyl]amine, 2-amino-2-methyl-1,3-propanediol (AMPD) and 2-amino-2-hydroxymethyl-1,3-propanediol.

In the compositions according to the present invention the amount of water is generally between 15 and 96.5% weight percent relative to the total weight of the composition.

When the composition is of the hydroalcoholic type the alcohol amount is generally less than 30 weight percent relative to the total weight of the composition and preferably between 1 and 15 percent. Among useable alcohols preferably employed are alcohols having 2 to 5 carbon atoms and are, particularly, ethanol, isopropanol, or butanol.

The cosmetic compositions for setting the hair according to the present invention are principally present in the form of an aerosol lacquer, a setting lotion by manual pulverization, a setting lotion or even a covering foam.

The cosmetic compositions for setting the hair, according to the present invention, can also contain a plasticizing agent in an amount between 0.01 and 16 percent by weight relative to the total weight of the composition.

Among the plasticizing agents being able to be employed in accordance with the present invention the following are mentioned:

CARBITOLS of Union Carbide namely CARBITOL® or diethylene glycol ethylether; METHYL CARBITOL® or diethylene glycol methylether; BUTYL CARBITOL® or diethylene glycol butylether; or also HEXYL CARBITOL® or diethylene glycol hexylether;

CELLOSOLVES of Union Carbide namely CELLOSOLVE® or ethylene glycol ethylether; BUTYL CELLOSOLVE® or ethylene glycol butylether; and HEXYL CELLOSOLVE® or ethylene glycol hexylether;

propylene glycol derivatives and in particular propylene glycol phenylether; propylene glycol diacetate; dipropylene glycol butylether; tripropylene glycol butylether;

as well as the DOWANOLS® of Dow Chemical namely DOWANOL PM® or propylene glycol methylether; DOWANOL DPM® or dipropylene glycol methylether; and DOWANOL TPM® or tripropylene glycol methylether.

Also mentionable are:

diethylene glycol methylether or DOWANOL DM® of Dow Chemical, ricin oil oxyethylenated with 40 moles of ethylene oxide such as that sold by Rhone Poulenc under the name MULGOFEN EL-719®, benzylic alcohol, triethyl citrate, sold by Pfizer under the name CITROFLEX-2®.

1,3-butylene glycol, diethyl phthalate, dibutyl phthalate and diisopropyl phthalate, diethyl adipate, dibutyl adipate and diisopropyl adipate, diethyl tartrate and dibutyl tartrate, diethyl phosphate, dibutyl phosphate and 2-diethyl hexyl phosphate, and glycerol esters such as glycerol diacetate (diacetin) and glycerol triacetate (triacetine).

Various cosmetic additives can also be incorporated in the compositions according to the present invention such as solar filters; polymers having, preferably a molecular weight lower than or equal to 500,000 such as a reticulated homopolymer of methacryloyloxyethyltrimethyl ammonium chloride; and the reticulated copolymers of acrylamide and a monomer chosen among (i) neutralized 2-acid-2-acrylamide methyl sulfonic propane, (ii) ammonium acrylate and (iii) methacyloyloxyethyltrimethyl ammonium chloride; proteins; silicones; anti-foam agents; hydrating agents; humectants; perfumes; preservatives; colorants; antioxidants, etc.

Several examples of the cosmetic compositions for setting the hair are now set forth.

COMPOSITIONS EXAMPLES

Example 1

A setting spray is prepared in a service pump bottle:

| | |
|---|---|
| Hydrodispersible copolyester sold under the name AQ38® by Eastman Kodak | 3.0 g AM (active material) |
| Vinyl acetate/crotonic acid/4-tert-butyl vinyl benzoate (65/10/25) prepared according to Example 19 of French patent No. 78.30596 (No. 2,349,798) neutralized to 100 percent by 2-amino-2-methyl 1-propanol | 0.6 g |
| Dipropylene glycol methylether | 1.8 g |
| Water, sufficient amount for | 100 g |

The container, once filled, is then equipped with a spray pump.

After spraying the hair and drying, good hair setting and good hair holding together are achieved.

The lacquer is easily removed during shampooing and the hair possesses good shine.

Example 2

A setting spray is prepared by producing the following mixture:

| | |
|---|---|
| Hydrodispersible copolyester, sold under the name AQ 38® by Eastman Kodak | 5.0 g (AM) |
| Vinyl acetate/crotonic acid/4-tert-butylvinyl benzoate (65/10/25) prepared according to Example 19 of French patent No. 78.30596 (No. 2,349,798) neutralized 100% by potash | 1.0 g |
| Triethyl citrate | 0.6 g |
| Ethyl alcohol | 5.0 g |
| Water, sufficient amount for | 100 g |

The resulting lotion is then conditioned in a rechargeable spray diffuser in compressed air.

After spraying, drying is rapid and excellent hair holding together is obtained. The polymer film is easily removed during shampooing.

Example 3

An aerosol lacquer for the hair is prepared by conditioning in an appropriate aerosol container:

| | |
|---|---|
| Hydrodispersible copolyester, sold under the name AQ 38® by Eastman Kodak | 2.00 g (AM) |
| Vinyl acetate/crotonic acid/4-tert-butylvinyl benzoate (65/10/25) copolymer prepared according to Example 19 of French patent No. 78.30596 (No. 2,349,798) neutralized 100 percent by 2-amino-2-methyl-1-propanol | 0.50 g |
| Ricin oil oxyethylenated with 40 moles of ethylene oxide, sold under the name, MULGOFEN EL-719® by Rhone-Poulenc | 0.25 g |
| Dimethyl ether | 25.00 g |
| Water, sufficient amount for | 100 g |

The valve of the hair setter is attached and the container is hermetically closed. The lacquer applied onto the hair rapidly drys, possesses a good cosmetic touch and is easily removed during shampooing.

Example 4

In accordance with the same operating method as described in Example 1, a hair setting spray having the following composition is prepared in a pump bottle:

| | |
|---|---|
| Hydrodispersible copolyester, sold under the name AQ 55® by Eastman Kodak | 10.0 g (AM) |
| Vinyl acetate/crotonic acid/4-tert-butylvinyl benzoate (65/10/25) copolymer prepared according to Example 19 of French patent No. 78.30596 (No. 2,349,798) neutralized 100 percent by 2-amino-2-methyl-1-propanol | 1.5 |
| Water, sufficient amount for | 100 g |

After spraying, the lacquer exhibited good holding and is easily removed during shampooing.

COMPARATIVE EXAMPLES

In accordance with the same operating method as described in Example 1, three hair setting sprays (A, B and C) having the following compositions were prepared:

Spray A (in accordance with the present invention)

| Hydrodispersible copolyester, sold under the name AQ 38® by Eastman Kodak | 8.0 g (AM) |
|---|---|
| Vinyl acetate/crotonic acid/4-tert-butylvinyl benzoate (65/10/25) copolymer prepared according to Example 19 of French patent No. 78.30596 (No. 2,349,798) neutralized 100 percent by 2-amino-2-methyl-1-propanol | 1.6 g |
| Water, sufficient amount for | 100 g |

Spray B (comparative)

| Hydrodispersible copolyester, sold under the name, AQ 38® by Eastman Kodak | 8.0 g (AM) |
|---|---|
| Vinyl acetate/crotonic acid (90/10) copolymer, sold under the name LUVISET CA 66® by BASF, neutralized 100 percent by 2-amino-2-methyl-1-propanol | 1.6 g |
| Water, sufficient amount for | 100 g |

Spray C (comparative)

| Hydrodispersible copolyester, sold under the name AQ 38® by Eastman Kodak | 8.0 (AM) |
|---|---|
| Vinyl acetate/crotonic acid/vinyl neodecanoate, sold under the name, RESINE 28-29-30® by National Starch, neutralized 100 percent by 2-amino-2-methyl-1-Propanol | 1.6 g |
| Water, q.s.p. | 100 g |

A control spray (Spray D) is also prepared and only contains water.

Sprays B and C differ from the present invention's Spray A by the nature of the employed hydrosoluble copolymer.

On samples having a 22.5 cm length and for each spray, five times ten spray strokes are effected, the spray pump delivering a dose of 190 µl per spray. After air drying, the sample is soaked in a shampooing solution, rinsed, then is wound at a humid state on a 20 mm diameter hair curler. The sample is then dried under a hood, allowed to cool, unrolled and then vertically suspended. The length of the sample is then measured at time zero (t=0) then measured again 12 hours later (t=12 hours).

The following results were obtained:

TABLE A

| Sample No. | Spray | Length t = 0 | Length t = 12 hours |
|---|---|---|---|
| 1 | A | 9 cm | 13 cm |
| 2 | B | 5 cm | 7 cm |
| 3 | C | 8 cm | 9 cm |
| 4 | D (Control) | 9 cm | 14 cm |

It is noted that the lengths measured for Sample 1 treated by Spray A, that is to say with the composition according to the present invention, are analogous to those measured on Sample No. 4, treated with control Spray D.

This then signifies that the film obtained after drying Spray A, in accordance with the present invention, is perfectly eliminated at shampooing since there is no difference with control Spray D.

The lengths measured on Samples No. 2 and 3, that is to say after application of Sprays B and C, are clearly less than those measured after application of Spray D. This demonstrates that the films obtained after drying these compositions are not totally removed during soaking in the shampoo solution so that the samples preserve then more form which is given by rolling around the hair curler.

It is verified then that only the association, according to the present invention, constituted by a hydrodispersible copolyester and a particular hydrosoluble copolymer of formula (I) above, permits to lead to hair setting compositions exhibiting excellent removal during shampooing.

We claim:

1. An aqueous cosmetic composition for setting the hair, comprising in an aqueous or weakly hydroalcoholic medium.

(a) 0.5 to 40 percent by weight, relative to the total weight of said composition, of a hydrodispersible polycondensate having sulfonate functions, and (b) 0.5 to 15 percent by weight, relative to the total weight of said composition, of a hydrosoluble copolymer having the formula

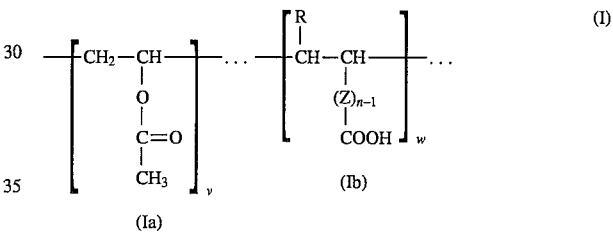

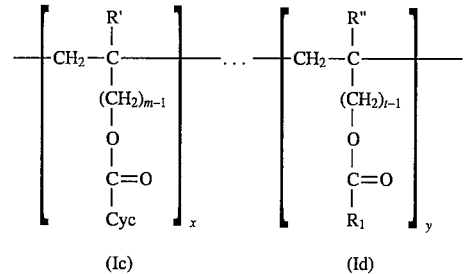

wherein

R, R' and R", each independently, represent hydrogen or methyl, m, n and t are 1 or 2, $R_1$ represents linear or branched, saturated or unsaturated alkyl having 2 to 21 carbon atoms, Z represents a divalent radical selected from the group consisting of —$CH_2$—, —$CH_2$—O—$CH_2$ and —$CH_2O$—$(CH_2)_2$— and Cyc represents a member selected from the group consisting of

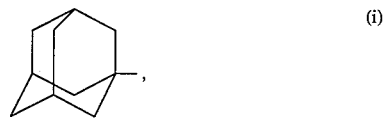

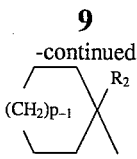

(ii)

wherein
$R_2$ represents hydrogen or methyl and
p is 1 or 2

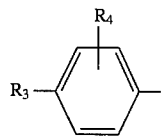

(iii)

wherein
$R_3$ represents hydrogen, methyl, ethyl, tert-butyl, ethoxy, butoxy or dodecyloxy and
$R_4$ represents hydrogen, alkyl having 1–4 carbon atoms or alkoxy having 1–4 carbon atoms, and

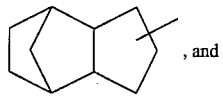

, and (iv)

v represents 10 to 91 weight percent,
w represents 3 to 20 weight percent,
x represents 4 to 60 weight percent, and
y represents 0 to 40 weight percent,
v+w+x+y being equal to 100 percent,
the said carboxylic acid functions of said copolymer being neutralized by a basic agent in an amount greater than 80 percent.

2. The cosmetic composition of claim 1 where, in the hydrosoluble copolymer of formula I, v represents 36 to 84 weight percent, w represents 6 to 12 weight percent, x represents 6 to 4 weight percent, and y represents 4 to 30 weight percent.

3. The cosmetic composition of claim 1 wherein the weight ratio between the said hydrosoluble copolymer and the said hydrodispersible polycondensate is between 0.15 and 0.6.

4. The cosmetic composition of claim 1 wherein the weight ratio between the said hydrosoluble copolymer and the said hydrodispersible polycondensate is between 0.2 and 0.4.

5. The cosmetic composition of claim 1 wherein said hydrodispersible polycondensate has a vitreous transition temperature between 10° C. and 100° C.

6. The cosmetic composition of claim 1 wherein said hydrodispersible polycondensate has a vitreous transition temperature ranging from 25° C. to 60° C.

7. The cosmetic composition of claim 1 wherein said hydrodispersible polycondensate having sulfonate functions is a copolyester or a copolyesteramide.

8. The cosmetic composition of claim 7 wherein the said copolyester results from the polycondensation of at least one dicarboxylic acid or an ester thereof, at least one diol and at least one difunctional sulfoaryldicarboxylic compound substituted on the aromatic ring by a —$SO_3M$ group wherein M represents hydrogen or a metallic ion selected from the group consisting of $Na^+$, $Li^+$ and $K^+$.

9. The cosmetic composition of claim 7 wherein said copolyesteramide results from the polycondensation of at least one dicarboxylic acid or an ester thereof, at least one diol, at least one sulfoaryldicarboxylic difunctional compound substituted on the aromatic ring by the group —$SO_3M$ wherein M represents hydrogen or a metallic ion selected from the group consisting of $Na^+$, $Li^+$ and $K^+$ and at least one diamine or an amino alcohol or a mixture thereof.

10. The cosmetic composition of claim 1 wherein the said hydrodispersible polycondensate includes at least units resulting from the polycondensation of isophthalic acid, sulfoaryldicarboxylic acid salt and diethyleneglycol.

11. The cosmetic composition of claim 10 wherein said hydrodispersible polycondensate is a copolyester further containing units resulting from the polycondensation of 1–4 cyclohexanedimethanol.

12. The cosmetic composition of claim 10 wherein said hydrodispersible polycondensate is a copolyester further containing units resulting from the polycondensation of a member selected from the group consisting of ethyleneglycol, triethyleneglycol, tetraethylene glycol and terephthalate.

13. The cosmetic composition of claim 1 wherein said carboxylic acid functions of said hydrosoluble copolymer are neutralized with a basic agent selected from the group consisting of soda, potash, 2-amino-2-methyl-1-propanol (AMP), triethanolamine, triisopropanolamine (TIPA), monoethanolamine, diethanolamine, tri[(2-hydroxy) 1-propyl] amine, 2-amino-2-methyl-1,3-propanediol (AMPD) and 2-amino-2-hydroxymethyl-1,3-propanediol.

14. The cosmetic composition of claim 1 wherein said composition contains a weakly hydroalcoholic medium, the alcohol content being lower than 30 weight percent relative to the total weight of said composition.

15. The cosmetic composition of claim 14 wherein the amount of alcohol ranges from 1 to 15 percent by weight relative to the total weight of said composition.

16. The cosmetic composition of claim 1 also containing at least one plasticizing agent in an amount ranging from 0.01 to 16 percent.

17. The cosmetic composition of claim 1 which also contains an additive selected from the group consisting of a solar filter, a polymer, a protein, a silicone, an anti-foam agent, a hydrating agent, a humectant, a perfume, a preservative, a dye and an anti-oxidant agent.

* * * * *